(12) United States Patent
Ostrovsky et al.

(10) Patent No.: US 9,271,754 B2
(45) Date of Patent: Mar. 1, 2016

(54) MOVABLE CURVED NEEDLE FOR DELIVERING IMPLANTS AND METHODS OF DELIVERING IMPLANTS

(75) Inventors: Isaac Ostrovsky, Wellesley, MA (US); Michael S. H. Chu, Brookline, MA (US); Jozef Slanda, Milford, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 743 days.

(21) Appl. No.: 13/313,963

(22) Filed: Dec. 7, 2011

(65) Prior Publication Data
US 2012/0158009 A1 Jun. 21, 2012

Related U.S. Application Data

(60) Provisional application No. 61/423,823, filed on Dec. 16, 2010.

(51) Int. Cl.
A61B 17/04 (2006.01)
A61B 17/34 (2006.01)
A61M 37/00 (2006.01)

(52) U.S. Cl.
CPC ........ *A61B 17/3468* (2013.01); *A61M 37/0069* (2013.01)

(58) Field of Classification Search
CPC .......... A61M 37/0069; A61B 17/3468; A61B 17/00; A61B 17/04
USPC .......................................... 606/144, 146, 148
See application file for complete search history.

(56) References Cited

U.S. PATENT DOCUMENTS

| | | | |
|---|---|---|---|
| 3,946,740 A | * | 3/1976 | Bassett .......................... 606/145 |
| 4,373,530 A | | 2/1983 | Kilejian |
| 4,541,427 A | | 9/1985 | Koss |
| 5,337,736 A | | 8/1994 | Reddy |
| 5,362,294 A | | 11/1994 | Seitzinger |
| 5,364,408 A | * | 11/1994 | Gordon .......................... 606/144 |
| 5,383,904 A | | 1/1995 | Totakura et al. |
| 5,507,754 A | | 4/1996 | Green et al. |
| 5,549,617 A | | 8/1996 | Green et al. |
| 5,562,689 A | | 10/1996 | Green et al. |
| 5,603,718 A | | 2/1997 | Xu |
| 5,611,515 A | | 3/1997 | Benderev et al. |

(Continued)

FOREIGN PATENT DOCUMENTS

| | | |
|---|---|---|
| EP | 0315371 A2 | 5/1989 |
| EP | 2033583 A1 | 3/2009 |

(Continued)

OTHER PUBLICATIONS

Search Report and Written Opinion for International Application No. PCT/US2011/064451, mailed Jun. 28, 2012, 19 pages.
Search Report and Written Opinion for International Application No. PCT/US2012/053105, mailed Dec. 11, 2012, 22 pages.
Non-Final Office Action for U.S. Appl. No. 13/598,143, mailed on Jul. 14, 2014, 17 pages.
Non-Final Office Action Response for U.S. Appl. No. 13/598,143, filed Oct. 14, 2014, 7 pages.

(Continued)

*Primary Examiner* — Victor Nguyen
(74) *Attorney, Agent, or Firm* — Brake Hughes Bellermann LLP

(57) ABSTRACT

In one general aspect, a medical device can include a base having a guide and a handle. The medical device can also include a needle member that has a curved portion and a handle portion. The curved portion of the needle member can be configured to slidably move within the guide of the base from a first position to a second position different than the first position when the handle portion of the needle member is moved towards the handle of the base.

14 Claims, 12 Drawing Sheets

(56) References Cited

U.S. PATENT DOCUMENTS

| | | |
|---|---|---|
| 5,628,757 A | 5/1997 | Hasson |
| 5,667,488 A | 9/1997 | Lundquist et al. |
| 5,817,074 A | 10/1998 | Racz |
| 5,840,011 A | 11/1998 | Landgrebe et al. |
| 5,899,909 A | 5/1999 | Claren et al. |
| 5,928,244 A | 7/1999 | Tovey et al. |
| 5,928,252 A | 7/1999 | Steadman et al. |
| 5,934,283 A | 8/1999 | Willem et al. |
| 5,964,732 A | 10/1999 | Willard |
| 6,010,447 A | 1/2000 | Kardjian |
| 6,042,534 A | 3/2000 | Gellman et al. |
| 6,042,536 A | 3/2000 | Tihon et al. |
| 6,056,688 A | 5/2000 | Benderev et al. |
| 6,074,395 A | 6/2000 | Trott et al. |
| 6,110,101 A | 8/2000 | Tihon et al. |
| 6,117,067 A | 9/2000 | Gil-Vernet |
| 6,221,005 B1 | 4/2001 | Bruckner et al. |
| 6,245,082 B1 | 6/2001 | Gellman et al. |
| 6,264,676 B1 | 7/2001 | Gellman et al. |
| 6,273,852 B1 | 8/2001 | Lehe et al. |
| 6,306,079 B1 | 10/2001 | Trabucco |
| 6,328,686 B1 | 12/2001 | Kovac |
| 6,368,859 B1 | 4/2002 | Atala |
| 6,382,214 B1 | 5/2002 | Raz et al. |
| RE37,815 E | 8/2002 | Rizvi |
| 6,475,139 B1 | 11/2002 | Miller |
| 6,502,578 B2 | 1/2003 | Raz et al. |
| 6,506,190 B1 | 1/2003 | Walshe |
| 6,533,795 B1 * | 3/2003 | Tran et al. ............. 606/144 |
| 6,575,897 B1 | 6/2003 | Ory et al. |
| 6,575,998 B2 | 6/2003 | Beyar |
| 6,595,911 B2 | 7/2003 | LoVuolo |
| 6,596,001 B2 | 7/2003 | Stormby et al. |
| 6,596,011 B2 | 7/2003 | Johnson et al. |
| 6,612,977 B2 | 9/2003 | Staskin et al. |
| 6,638,210 B2 | 10/2003 | Berger |
| 6,638,211 B2 | 10/2003 | Suslian et al. |
| 6,641,524 B2 | 11/2003 | Kovac |
| 6,641,525 B2 | 11/2003 | Rocheleau et al. |
| 6,648,921 B2 | 11/2003 | Anderson et al. |
| 6,652,450 B2 | 11/2003 | Neisz et al. |
| 6,666,817 B2 | 12/2003 | Li |
| 6,673,010 B2 | 1/2004 | Skiba et al. |
| 6,689,047 B2 | 2/2004 | Gellman |
| 6,691,711 B2 | 2/2004 | Raz et al. |
| 6,752,814 B2 | 6/2004 | Gellman et al. |
| 6,755,781 B2 | 6/2004 | Gellmann |
| 6,755,843 B2 | 6/2004 | Chung et al. |
| 6,802,807 B2 | 10/2004 | Anderson et al. |
| 6,830,052 B2 | 12/2004 | Carter et al. |
| 6,911,003 B2 | 6/2005 | Anderson et al. |
| 6,932,759 B2 | 8/2005 | Kammerer et al. |
| 6,953,428 B2 | 10/2005 | Gellmann et al. |
| 6,960,160 B2 | 11/2005 | Browning |
| 6,971,986 B2 | 12/2005 | Staskin et al. |
| 7,037,255 B2 | 5/2006 | Inman |
| 7,056,333 B2 | 6/2006 | Walshe |
| 7,070,556 B2 | 7/2006 | Anderson |
| 7,070,558 B2 | 7/2006 | Gellman et al. |
| 7,083,568 B2 | 8/2006 | Neisz et al. |
| 7,112,171 B2 | 9/2006 | Rocheleau et al. |
| 7,131,943 B2 | 11/2006 | Kammerer |
| 7,175,591 B2 | 2/2007 | Kaladelfos |
| 7,198,597 B2 | 4/2007 | Siegel et al. |
| 7,204,802 B2 | 4/2007 | De Leval |
| 7,261,723 B2 | 8/2007 | Smith et al. |
| 7,267,645 B2 | 9/2007 | Anderson et al. |
| 7,291,104 B2 | 11/2007 | Neisz |
| 7,326,213 B2 | 2/2008 | Benderev et al. |
| 7,338,502 B2 | 3/2008 | Rosenblatt |
| 7,361,138 B2 | 4/2008 | Wagner et al. |
| 7,393,320 B2 | 7/2008 | Montpetit et al. |
| 7,410,460 B2 | 8/2008 | Benderev |
| 7,422,557 B2 | 9/2008 | Arnal et al. |
| 7,500,945 B2 | 3/2009 | Cox et al. |
| 7,556,598 B2 | 7/2009 | Rao |
| 7,611,454 B2 | 11/2009 | De Leval |
| 7,621,864 B2 | 11/2009 | Suslian et al. |
| 7,686,760 B2 | 3/2010 | Anderson et al. |
| 7,713,188 B2 | 5/2010 | Bouffier |
| 7,763,034 B2 | 7/2010 | Siegel et al. |
| 7,794,385 B2 | 9/2010 | Rosenblatt |
| 7,811,223 B2 | 10/2010 | Hodroff et al. |
| 7,828,715 B2 | 11/2010 | Haverfield |
| 8,709,021 B2 * | 4/2014 | Chu et al. ............. 606/144 |
| 2001/0049467 A1 | 12/2001 | Lehe et al. |
| 2003/0065337 A1 | 4/2003 | Topper et al. |
| 2004/0106847 A1 | 6/2004 | Benderev |
| 2004/0225305 A1 | 11/2004 | Ewers et al. |
| 2004/0225385 A1 | 11/2004 | Takagi et al. |
| 2004/0230206 A1 | 11/2004 | Gellman et al. |
| 2005/0101834 A1 | 5/2005 | Merade |
| 2005/0245787 A1 | 11/2005 | Cox et al. |
| 2006/0058780 A1 | 3/2006 | Edwards et al. |
| 2006/0063968 A1 | 3/2006 | Anderson et al. |
| 2006/0069301 A1 | 3/2006 | Neisz et al. |
| 2006/0142637 A1 | 6/2006 | Gill |
| 2006/0173468 A1 | 8/2006 | Simmon et al. |
| 2006/0195007 A1 | 8/2006 | Anderson et al. |
| 2006/0217589 A1 | 9/2006 | Wan et al. |
| 2006/0235262 A1 | 10/2006 | Arnal et al. |
| 2006/0258898 A1 | 11/2006 | Montpetit et al. |
| 2006/0293554 A1 | 12/2006 | Crawford |
| 2007/0156012 A1 | 7/2007 | Tracey et al. |
| 2007/0173599 A1 | 7/2007 | Liu et al. |
| 2007/0173864 A1 | 7/2007 | Chu |
| 2007/0249936 A1 | 10/2007 | Deckman et al. |
| 2007/0249939 A1 | 10/2007 | Gerbi et al. |
| 2008/0004487 A1 | 1/2008 | Haverfield |
| 2008/0009914 A1 | 1/2008 | Buysman et al. |
| 2008/0021263 A1 | 1/2008 | Escude et al. |
| 2008/0076963 A1 | 3/2008 | Goria |
| 2008/0082121 A1 | 4/2008 | Chu |
| 2008/0091058 A1 | 4/2008 | Bosley et al. |
| 2008/0097329 A1 | 4/2008 | Hodroff et al. |
| 2008/0154087 A1 | 6/2008 | Wagner et al. |
| 2008/0167520 A1 | 7/2008 | Benderev |
| 2008/0188890 A1 | 8/2008 | Weitzner et al. |
| 2008/0200751 A1 | 8/2008 | Browning |
| 2008/0255563 A1 | 10/2008 | Farr et al. |
| 2009/0023978 A1 | 1/2009 | Arnal et al. |
| 2009/0048479 A1 | 2/2009 | Goria |
| 2009/0062819 A1 | 3/2009 | Burkhart et al. |
| 2009/0088599 A1 | 4/2009 | Zook et al. |
| 2009/0137861 A1 | 5/2009 | Goldberg et al. |
| 2009/0137862 A1 | 5/2009 | Evans et al. |
| 2009/0143637 A1 | 6/2009 | Raz et al. |
| 2009/0149700 A1 | 6/2009 | Garcia et al. |
| 2009/0177026 A1 | 7/2009 | Goldman |
| 2009/0216072 A1 | 8/2009 | Zipper |
| 2009/0221868 A1 | 9/2009 | Evans |
| 2009/0240104 A1 | 9/2009 | Ogdahl et al. |
| 2009/0264698 A1 | 10/2009 | Arnal et al. |
| 2009/0276038 A1 | 11/2009 | Tremulis et al. |
| 2009/0287229 A1 | 11/2009 | Ogdahl |
| 2009/0306464 A1 | 12/2009 | Griguol |
| 2010/0030016 A1 | 2/2010 | Knoll |
| 2010/0113866 A1 | 5/2010 | Goldman |
| 2010/0113867 A1 | 5/2010 | Wiles et al. |
| 2010/0113868 A1 | 5/2010 | Goldman |
| 2010/0137888 A1 | 6/2010 | Wulc et al. |
| 2010/0191046 A1 | 7/2010 | Gobron et al. |
| 2010/0217069 A1 | 8/2010 | Meade et al. |
| 2010/0261952 A1 | 10/2010 | Montpetit et al. |
| 2010/0261955 A1 | 10/2010 | O'Hern et al. |
| 2010/0274074 A1 | 10/2010 | Khamis et al. |
| 2010/0305581 A1 | 12/2010 | Hart |
| 2011/0160529 A1 | 6/2011 | Crawford |
| 2013/0060261 A1 | 3/2013 | Ostrovsky et al. |

FOREIGN PATENT DOCUMENTS

| | | |
|---|---|---|
| EP | 2001398 B1 | 5/2010 |
| EP | 2255733 A1 | 12/2010 |

(56) References Cited

FOREIGN PATENT DOCUMENTS

| WO | 96/39948 A1 | 12/1996 |
| WO | 2007109062 A2 | 9/2007 |
| WO | 2008097665 A1 | 8/2008 |
| WO | 2009018372 A3 | 2/2009 |
| WO | 2013/033373 A1 | 3/2013 |

OTHER PUBLICATIONS

Final Office Action for U.S. Appl. No. 13/598,143, mailed Feb. 4, 2015, 20 pages.
Final Office Action Response for U.S. Appl. No. 13/598,143, filed Apr. 1, 2015, 8 pages.

* cited by examiner

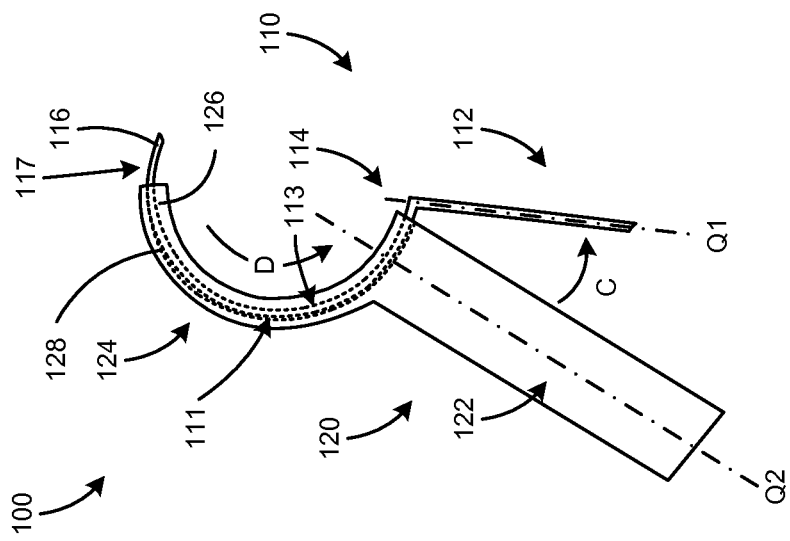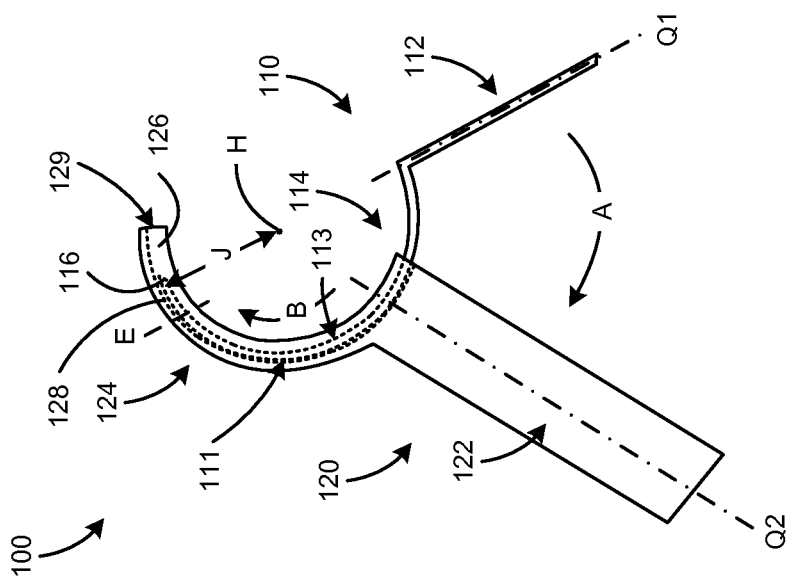

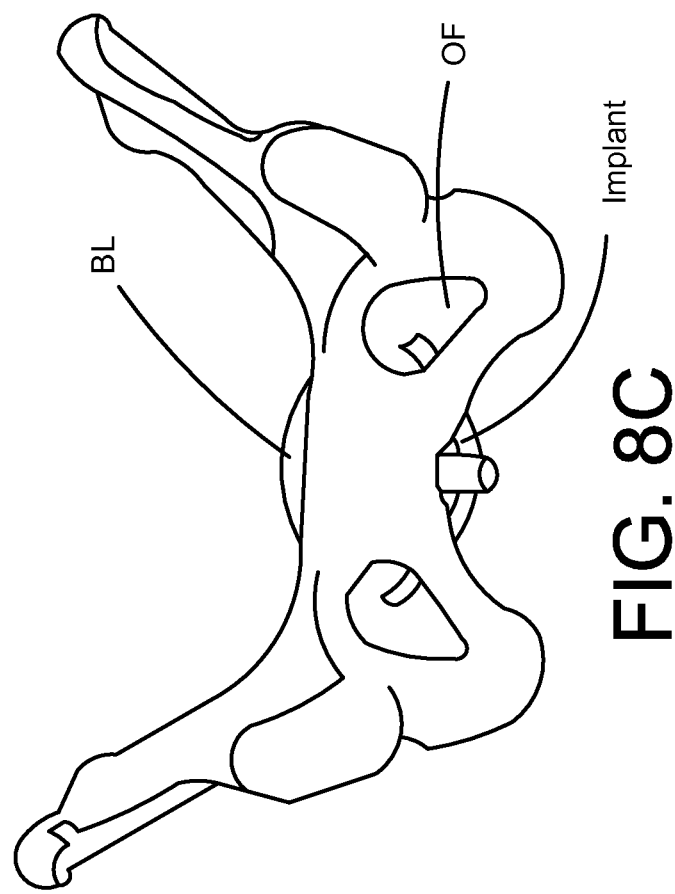

MOVABLE CURVED NEEDLE FOR DELIVERING IMPLANTS AND METHODS OF DELIVERING IMPLANTS

CROSS REFERENCE TO RELATED APPLICATION

This application is a Nonprovisional of, and claims priority to, U.S. Provisional Application No. 61/423,823, filed on Dec. 16, 2010, entitled "MOVABLE CURVED NEEDLE FOR DELIVERING IMPLANTS AND METHODS OF DELIVERING IMPLANTS", which is incorporated by reference herein in its entirety.

TECHNICAL FIELD

This disclosure relates generally to medical devices and more particularly to medical devices that are configured to place or deliver implants within a body of a patient.

BACKGROUND

A variety of medical procedures are performed to provide support to portions of a body of a patient. For example, some medical procedures are performed to treat various female pelvic dysfunctions, including procedures to treat urinary incontinence, and correcting various prolapse conditions such as uterine prolapse, cystoceles, rectoceles, and vaginal vault prolapse.

Some such medical procedures have included placing implants within the pelvic region of the patient. Some of the implants are delivered to the pelvic region of the patient through one or more vaginal incisions, and/or through exterior incisions in the patient.

Often such implants are delivered or placed within the body of the patient using an insertion or delivery tool. The insertion tools used to deliver the implants within a body of a patient typically include a curved portion and a sharp needle or point at one end. Some of the insertion tools used to deliver the implants can be uncontrollable and can deviate from the desired direction during the implantation process. Also, some of the insertion tools used to deliver the implants have large needles that can cause undesirable levels of trauma to tissues during the implantation process. Accordingly, complications, such as inadvertent tissue, nerve, bladder, or uretheral damage can occur during the implantation process. Such complications can also occur if the shape or curvature of the insertion tool is inappropriate for delivering the implant to the desired location within the body of the patient. Thus, it would be desirable to provide an insertion tool that may be used to deliver an implant to a location within a body of a patient without damaging tissue and/or adjacent nerves or organs in an undesirable fashion.

SUMMARY

In one general aspect, a medical device can include a base having a guide and a handle. The medical device can also include a needle member that has a curved portion and a handle portion. The curved portion of the needle member can be configured to slidably move within the guide of the base from a first position to a second position different than the first position when the handle portion of the needle member is moved towards the handle of the base.

BRIEF DESCRIPTION OF THE DRAWINGS

FIGS. 1A and 1B are schematic diagrams of a medical device, according to an embodiment.

FIGS. 8A, 8B, and 8C schematically illustrate implants disposed within a body of a patient.

DETAILED DESCRIPTION

Figure 1E:
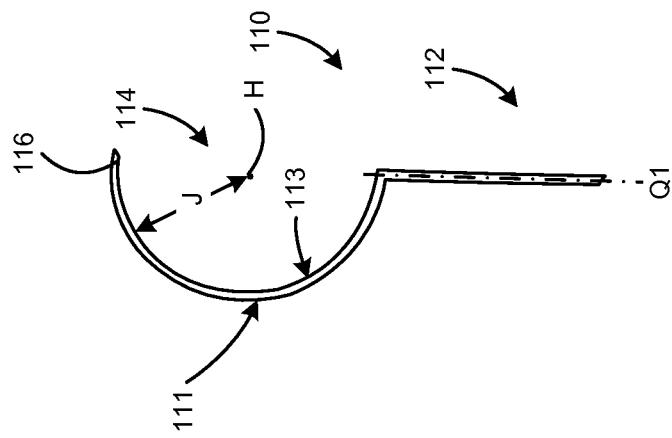
FIG. 1E is a schematic diagram that illustrates a needle member of the medical device shown in FIGS. 1A and 1B.

The devices and methods described herein are generally directed to insertion or delivery tools for placing implants within a body of a patient. The implants delivered with the insertion or delivery tools may be used in any portion of a body of a patient. In some embodiments, the implants include, but are not limited to, implants that are placed within a pelvic region of a patient. For example, the implants that may be placed with the disclosed insertion or delivery tools include posterior support implants, anterior support implants, and/or total pelvic floor repair implants. Such implants can be placed into the pelvic space of a patient and secured at any of several locations within the pelvic space to treat many different pelvic floor dysfunctions. For example, an implant can be secured to a sacrospinous ligament or a ureterosacral ligament for uterine preservation (e.g., if a prolapsed uterus is otherwise healthy, a hysterectomy is not preformed and the uterus is re-suspended with an implant), or for posterior support. In another embodiment, an implant can be secured to pubo-urethral tissue or an obturator muscle (e.g., internus or externus) and/or membrane (each also referred to herein as "obturator") to treat, for example, incontinence. In yet another embodiment, an implant can be secured to a sacrospinous ligament or an arcus tendineus fascia pelvis (i.e., white line) (also referred to herein as "arcus tendineus") for paravaginal repairs including, for example, cystoceles, rectoceles and enteroceles. An implant can also be secured to various combinations of such locations. The insertion tools, implants, and procedures described herein may be used in a female patient or a male patient.

In some embodiments, the disclosed insertion or delivery tool(s) may be used to place an implant, for example, through a vaginal incision, in a retro-pubic direction (behind the pubic bone), or in a pre-pubic direction (in front of the pubic bone). In other embodiments, an implant can be placed in the direction of other anatomical structures or tissues as desired. A procedure to deploy a pelvic implant can include vaginal incisions, such as an anterior vaginal incision and/or an anterior vaginal incision. In some embodiments, a procedure may include an exterior incision.

As used herein, the terms proximal portion or proximal end refer to the portion or end, respectively, of a device that is closest to a physician when performing a medical procedure, and the terms distal portion or distal end refer to the portion or end, respectively, of the device that is furthest from the physician during a medical procedure. For example, a distal end or portion of an insertion tool or device as described herein refers to the end or portion of the device that is first inserted into a body of a patient during a medical procedure. The proximal end or portion is the end or portion of the device that is remains outside of the body of the patient during the insertion procedure (or if the entire device is inserted into the body of the patient during the delivery procedure, the proximal end portion is inserted into a body of the patient after the distal end or distal portion is inserted). The terms "trailing end" and "leading end" are also referred to herein and have similar meanings as proximal and distal, respectively. As used herein, the term "leading end" refers to the end of a device or apparatus that is inserted into a body first. The term "trailing end" refers to the end of the device or apparatus that remains outside of the body of the patient or is inserted into the body after the leading end.

Various embodiments of insertion or delivery tools are described herein. The insertion or delivery tool may be used to deliver a variety of different implants into the body of a patient and only some examples of implants are described herein.

FIGS. 1A and 1B are schematic diagrams of a medical device 100, according to an embodiment. The medical device 100 is configured to be used as an insertion tool or delivery tool to implant or insert a bodily implant (not shown) into a body of a patient. The medical device 100 may be used to insert any type of implant into a body of a patient. In some embodiments, the medical device 100 can be configured to place an implant into a pelvic region of a patient. Specifically, in some embodiments, the medical device 100 is configured to place an implant through an obturator muscle and/or a membrane of a patient.

As shown in FIG. 1A, the medical device 100 includes a needle member 110 that is movable with respect to a base 120. Specifically, the needle member 110 has a curved portion 114 configured to move (e.g., slidably move) in direction B within a guide 124 of the base 120 from a first position or configuration shown in FIG. 1A to a second position or configuration shown in FIG. 1B. The curved portion 114 of the needle member 110 is slidably moved within the guide 124 of the base 120 when a handle portion of the needle member 110 is moved towards (e.g., translated towards, rotatably moved towards) a handle 122 of the base 120 in direction A. As shown in FIG. 1A, the guide 124 has a curved shape, and the guide 124 can, in some embodiments, be referred to as a curved guide.

As shown in FIG. 1A, the needle member 110 has a distal tip 116 at a distal end portion of the curved portion 114 of the needle member 110. When the medical device 100 is in the first position or configuration shown in FIG. 1A, the distal tip 116 is disposed within the guide 124 of the base 120, and when the medical device 100 is in the second position or configuration shown in FIG. 1B, the distal tip 116 is moved out of the guide 124 of the base 120. In other words, when the medical device 100 is in the second configuration, the distal tip 116 is disposed outside of the guide 124. Thus, the distal tip 116 can be moved out of the guide 124 when the curved portion 114 is slidably moved along direction B from the first configuration shown in FIG. 1A to the second configuration shown in 1B. In some embodiments, the first configuration can be referred to as a stowed configuration because the distal tip 116 is disposed within the guide 124 of the base 120, and the second configuration can be referred to as a deployed configuration because a distal portion 117 that includes the distal tip 116 is moved outside of the guide 124 of the base 120. In some embodiments, the stowed configuration can be referred to as a retracted configuration, and the deployed configuration can be referred to as an extended configuration.

In some embodiments, the distal tip 116 of the curved portion 114 can be configured to cut or pierce a bodily tissue. For example, in some embodiments, the distal tip 116 can include a sharp portion. In some embodiments, the distal tip 116 can define a blunt end. In some embodiments, the distal tip 116 can define a dilating end configured to dilate a tissue of a patient.

As shown in FIGS. 1A and 1B, the handle portion 112 of the needle member 110 is aligned along a longitudinal axis Q1 and the handle 122 of the base 120 is aligned along a longitudinal axis Q2. As shown in FIG. 1A, a first acute angle is defined by the longitudinal axis Q1 of the handle portion 112 of the needle member 110 and the longitudinal axis Q2 of the handle 122 of the base 120 when the medical device 100 is in the stowed configuration. As shown in FIG. 1B, a second acute angle, that is smaller than the first acute angle, is defined by the longitudinal axis Q1 of the handle portion 112 of the needle member 110 and the longitudinal axis Q2 of the handle 122 of the base 120 when the handle portion 112 of the needle member 110 is moved towards the handle 122 of the base 120 to define the deployed configuration of the medical device 100. Thus, an angle between longitudinal axis Q1 of the handle portion 112 and the longitudinal axis Q2 of the handle 122 decreases when the medical device 100 is moved from the stowed configuration (shown in FIG. 1A) to the deployed configuration (shown in FIG. 1B). It follows that the angle between longitudinal axis Q1 of the handle portion 112 and the longitudinal axis Q2 of the handle 122 increases when the medical device 100 is moved from the deployed configuration (shown in FIG. 1B) to the stowed configuration (shown in FIG. 1A).

Referring to FIG. 1B, the curved portion 114 of the needle member 110 can be slidably moved along direction D which is opposite direction B shown in FIG. 1A. In such embodiments, the curved portion 114 of the needle member 110 can be slidably moved when the handle portion 112 of the needle member 110 is moved away from the handle 122 of the base 120. Accordingly, the medical device 100 can be changed or moved from the deployed configuration shown in FIG. 1B to the stowed configuration shown in FIG. 1A. Thus, the medical device 100 can be reversibly moved to/from the deployed configuration or the stowed configuration. When the medical device 100 is moved from the deployed configuration to the stowed configuration, an angle between longitudinal axis Q1 of the handle portion 112 and the longitudinal axis Q2 of the handle 122 increases.

In some embodiments, the medical device 100 can be in the stowed configuration shown in FIG. 1A when being inserted into (e.g., when at least a leading or distal end of the medical device 100 is inserted into) a body of a patient and moved to the deployed configuration shown in FIG. 1B after being inserted in the body of the patient. Specifically, the medical device 100 can be in the stowed configuration shown in FIG. 1A so that the distal tip 116 of the needle member 110 may not come in contact with a bodily tissue of a patient (because the distal tip 116 will be disposed within the guide 124). After being inserted into the body of the patient, the medical device 100 can be moved to the deployed configuration so that the distal tip 116 of the needle member 110 may come in contact with (e.g., pierce) a bodily tissue of the patient. In some embodiments, a physician may apply a force (along direction A and about an axis) to the handle portion 112 of the needle member 110 so that the medical device 100 can be changed to the deployed configuration.

As mentioned above, in some embodiments, the medical device 100 may be used to insert an implant (e.g., a surgical implant) (not shown) into a pelvic region of a patient. In some embodiments, the distal tip 116 of the needle member 110 of the medical device 100 can be coupled to or associated with an implant. In some embodiments, the distal tip 116 of the needle member 110 of the medical device 100 can be coupled to or associated with the implant when in the stowed configuration and/or when in the deployed configuration. An example of an implant that can be used with the medical device 100 is shown in connection with FIG. 3.

As a specific example, while outside of a body of a patient and while in the deployed configuration, an implant can be coupled to the distal tip 116 of the needle member 110. The distal tip 116 of the needle member 110 can be retracted, while coupled to the implant (or at least a portion thereof), so that the medical device 100 is in the stowed configuration. The medical device 100 (e.g., the portion of the medical device 100 coupled to or associated with the implant) can then be inserted into a pelvic region of the patient while in the stowed configuration. In some embodiments, the medical device 100 (e.g., a distal end portion of the medical device 100) may be inserted into the pelvic region of the patient through an anterior vaginal incision (i.e., via an inside-out approach). In some embodiments, the medical device 100 can be inserted into the body of the patient such that a distal portion of the guide 124 of the base 120 is moved along an edge or in close proximity of an edge of a bone (e.g., a pelvic bone) of the patient while the medical device 100 is in the stowed configuration (while the distal tip 116 is disposed within the guide 124).

After the distal portion of the guide 124 is place in a desirable location with respect to, for example an obturator muscle and/or a membrane of a patient, the medical device 100 can be changed to the deployed configuration and the distal tip 116 of the needle member 110 can be extended and pierce through the obturator muscle or the membrane of the patient to place the implant coupled to the distal tip 116 of the needle member 110. In some embodiments, the medical device can be configured to place an implant around a bone defining an obturator of a patient. In some embodiments, the distal tip 116 of the needle member 110 can be configured to slidably move out of the guide 124 of the base 120 from a location inside of the body of the patient to a location outside of the body of the patient. In other words, the distal tip 116 of the needle member 110 can be pushed from within the guide 124 in the stowed configuration to the deployed configuration such that the distal tip 116 is disposed outside of the patient when in the deployed configuration. In some embodiments, once the medical device 100 has advanced the implant (or portion thereof) to the desired location within the body of the patient, the implant can be decoupled from the medical device 100. If the distal tip 116 of the needle member 110 is outside of the body of the patient, the portion of the implant coupled to the distal tip 116 can be decoupled from the distal tip 116.

After the implant has been placed in a desirable location, the medical device 100 can be withdrawn from the body of the patient to leave the implant in place within the body of the patient. In some embodiments, the medical device 100 can be moved to the stowed configuration shown in FIG. 1A (from the deployed configuration) before being retracted from the body of the patient. In some embodiments, the medical device 100 can be moved from the deployed configuration shown in FIG. 1B to the stowed configuration shown in FIG. 1A so that the tip 116 of the needle member 110 may be retracted after coming in contact with (e.g., piercing) a bodily tissue of a patient. More details related to coupling of an implant to a distal tip of the needle member of a medical device (e.g., medical device 100) during a medical procedure are described in connection with FIGS. 2A and 2B.

Because certain tissues of a patient (e.g., an obturator muscle) can be relatively stiff and/or relatively difficult to pierce, the guide 124 of the base 120 can function as a support for the curved portion 114 of the needle member 110 as the distal tip 116 is moved through the tissues. Specifically, the guide 124 of the base 120 can be made of a relatively rigid material that can prevent the curved portion 114 of the needle member 110 from bending in an undesirable fashion. In some embodiments, the guide 124 of the base 120 can support the curved portion 114 of the needle member 110 while the distal tip 116 is moved through a tissue so that the curved portion 114 of the needle member 110 may not be deformed inelastically.

Because the guide 124 of the base 120 can function as a support for the curved portion 114 of the needle member 110, the curved portion 114 of the needle member 110 can have a cross-sectional area (along a plane orthogonal (or approximately orthogonal) to a longitudinal axis of the needle member 110) that is smaller than would otherwise be permissible without the guide 124. In other words, the curved portion 114 of the needle member 110 can be relatively thin (e.g., can have a relatively small diameter) because only a relatively short portion (shown as distal portion 117) of the curved portion 114 of the needle member 110 may project from the guide 124.

In some embodiments, a distal end 129 of the guide 124 can be moved so that the distal end 129 is contacting or is close to (e.g., less than 2 mm, less than 2 cm) a tissue through which at least a portion of the distal portion 117 (e.g., the distal end 116) of the needle member 110 are to pierce when the medical device 100 is moved to the deployed configuration. Because the distal end 129 of the guide 124 can be contacting or close to the tissue that will be pierced by at least a portion of the distal portion 117 (e.g., the distal end 116) of the needle member 110, a length of the portion of the distal portion 117 can be nearly zero when the distal end 116 contacts the tissue as the medical device 100 is moved to the deployed configuration. Also, because the distal end 129 of the guide 124 can be contacting or close to the tissue that will be pierced by the distal portion 117 of the needle member 110, the rigidity of the distal portion 117 can be less than might otherwise be necessary when the distal portion 117 is projecting over a relatively long distance (e.g., over 5 cm, over 10 cm) without support from a guide such as guide 124.

In some embodiments, the diameter of the curved portion 114 of the needle member 110 can be less than 3 millimeters (mm). Specifically, the distal portion 117 that projects from the guide 124 can have a diameter of less than 3 mm. For example, in some embodiments, the curved portion 114 of the needle member 110 can have a diameter of approximately 1.5 mm. In some embodiments, the needle member 110 (e.g., the curved portion 114 of the needle member 110) can have a diameter less than 1.5 mm or a diameter greater than 1.5 mm.

As shown in FIG. 1A, the curved portion 114 of the needle member 110 can have a concave portion 111 (also can be referred to as an outside portion) that faces away from a centroid H of the curved portion 114. The curved portion 114 also can have a concave portion 113 (also can be referred to as an inner portion) that faces towards the centroid H of the curved portion 114. The curved portion 114 of the needle member 110 can be configured to slidably move within the guide 124 around the centroid H. In this embodiment, the centroid H is at a radius J of the curvature of the curved portion 114. As shown in FIG. 1A, the handle portion 112 of the needle member 110 can be configured to rotatably move about the centroid or axis H (which, in some embodiments, is at the radius J of the curvature of the curved portion 114) when the handle portion 112 is moved along direction A towards the handle 122 of the base 120. Said differently, the handle portion 112 can be configured to rotatably move about an axis at the centroid H. In this embodiment, the handle portion 112 of the needle member 110 can be configured to rotatably move within a plane that is orthogonal to, or substantially orthogonal to, an axis at the centroid H. The needle member 110 (or at least the curved portion 114 of the needle member 110) can be disposed within the plane, and the base 120 (or at least the guide 124 of the base 120) can also be disposed within the same plane. In some embodiments, the radius J can be between 1.0 inches to 2.0 inches (e.g., 1.2 inches, 1.5 inches, 1.7 inches). In some embodiments, the radius J can be less than 1.0 inch, or can be greater than 2.0 inches.

Although not shown in FIG. 1A, the curved portion 114 of the needle member 110 and guide 124 of the base 120 can have a helical curve. Thus, at least the curved portion 114 of the needle member 110 and the handle portion 112 of the needle member 110 may not be disposed within a common plane. Similarly, at least the guide 124 of the base 120 and the handle 122 of the base 120 may not be disposed within a common plane.

In this embodiment, the curved portion 114 of the needle member 110 is configured to slidably move within a channel 126 defined by the guide 124 of the base 120. A zoomed-in cross sectional view of the channel 126 defined by the guide 124 is shown in FIG. 1C. Specifically, FIG. 1C is a zoomed-in schematic illustration of the channel 126 defined by the guide 124 cut at line E shown in FIG. 1A.

As shown in FIG. 1C, the guide 124 defines the channel 126 within which the curved portion 114 of the needle member 110 can be disposed. The curved portion 114 of the needle member 110 can slidably move against an inner surface 128 of the guide 124 that defines the channel 126. Specifically, the curved portion 114 can slidably move against the inner surface 128 of the guide 124 when the handle portion 112 of the needle member 110 is moved towards the handle 122 of the base 120 along direction A (shown in FIG. 1A).

In this embodiment, the channel 126 has an upside-down U-shape. In some embodiments, the channel 126 can have a shape that is different than the upside-down U-shape shown in FIG. 1C. In some embodiments, the channel 126 of the guide 124 can have a cross-sectional shape of any type of polygon. For example, the channel 126 can have a square or rectangular cross-sectional shape (or outer profile) within which the curved portion 114 of the needle member 110 can be disposed. In some embodiments, the channel 126 can have a tapered shaped and/or a tapered portion (e.g., tapered from a proximal portion to a distal portion).

Also as shown in FIG. 1C, the curved portion 114 of the needle member 110 has a circular cross-sectional shape (or outer profile). In some embodiments, the curved portion 114 of the needle member 110 can have a different shape than a circular cross-sectional shape. In some embodiments, the curved portion 114 of the needle member 110 can have a cross-sectional shape (or outer profile) of any type of polygon. For example, the curved portion 114 of the needle member 110 can have a square or a rectangular cross-sectional shape (or outer profile). In some embodiments, the curved portion 114 can have a tapered shaped and/or a tapered portion (e.g., tapered from a proximal portion to a distal portion). In such embodiments, the curved portion 114 can have a varying diameter.

In some embodiments, the curved portion 114 of the needle member 110 can have a portion of a surface with a cross-sectional shape (or outer profile) that matches a portion of the inner surface 128 of the guide 124. For example, as shown in FIG. 1C a convex portion 111 of the surface of the curved portion 114 is approximately the same as at least a portion of the inner surface 128 of the channel 126. In some embodiments, the curved portion 114 of the needle member 110 can have a shape that does not match a shape of the channel 126 of the guide 124.

As shown in FIG. 1C, the curved portion 114 has a diameter F that is slightly smaller than a distance G defined by sidewalls 129 of the guide 124. In some embodiments, the diameter F of the curved portion 114 of the needle can be between 0.5 mm and 4 mm. The distance G defined by the sidewalls 129 of the guide 124 are only slightly larger than the diameter F of the curved portion 114 so that the curved portion 114 of the needle member 110 may not move to the left or to the right in an undesirable fashion when the curved portion 114 of the needle member 110 is advanced within the guide 124. In some embodiments, the distance G defined by the sidewalls 129 of the guide 124 may be smaller than the diameter F of the curved portion 114 of the needle member 110. In some embodiments, the distance G between the sidewalls 129 can vary (e.g., taper) along the length of the guide 124 (from a proximal portion of the guide 124 to a distal portion of the guide 124). In some embodiments, the width K of the guide 124 can be between 1 mm to a few centimeters (cm) (e.g., 2 cm, 4 cm).

As shown in FIG. 1C, the concave portion 113 of the curved portion 114 of the needle member 110 is exposed to an ambient environment around the guide 124. In other words, the concave portion 113 of the curved portion 114 of the needle member 110 is not covered by the guide 124.

In some embodiments, the guide 124 can have a portion that defines a lumen within which the curved portion 114 of the needle member 110 can be disposed. For example, although not shown in FIG. 1C, the guide 124 can define a portion that extends between the sidewalls 129 of the channel 126. The portion can be configured to prevent the curved portion 114 of the needle member 110 from moving (e.g., sliding) out of the channel 126 when the curved portion of the needle member 110 is slidably moved within the channel 126 of the guide 124. An example of a guide that has a portion that defines at least a portion of a lumen is described in connection with FIGS. 4A through 4C.

In some embodiments, the curved portion 114 of the needle member 110 can have a fixed curvature. In other words, the curved portion 114 of the needle member 110 can be constructed so that the curved portion 114 of the needle member 110 is relaxed (or biased) in a curved shape. Accordingly, the inner surface 128 of the guide 124 can be defined to match the curvature of the convex portion 111 of the curved portion 114 of the needle member 110. In other words, the inner surface 128 of the guide 124 can have a curvature that is approximately the same of the curvature of the convex portion 111 of the curved portion 114 of the needle member 110. Thus, in some embodiments, the radius of curvature of the guide 124 can be the same as or approximately the same as radius of curvature of the convex portion 111 of the curved portion 114 of the needle member 110.

In some embodiments, the radius J of the curvature of the curved portion 114 of the needle member 110 can be fixed. In other words, the radius J of the curvature of the curved portion 114 of the needle member 110 from approximately the distal tip 116 to a distal end of the handle portion 112 of the needle member 110 can be the same. In some embodiments, the radius J of the curvature of the curved portion 114 of the needle member 110 is substantially fixed.

In some embodiments, the radius of the curvature of the guide 124 can vary. In other words, in some embodiments, the guide 124 may not have a uniform radius of curvature. In some embodiments, the radius of the curvature of the curved portion 114 can vary from the distal tip 116 to a distal end of the handle portion 112 of the needle member 110. In other words, in some embodiments, the curved portion 114 may not have a uniform radius of curvature.

Figure 1D:
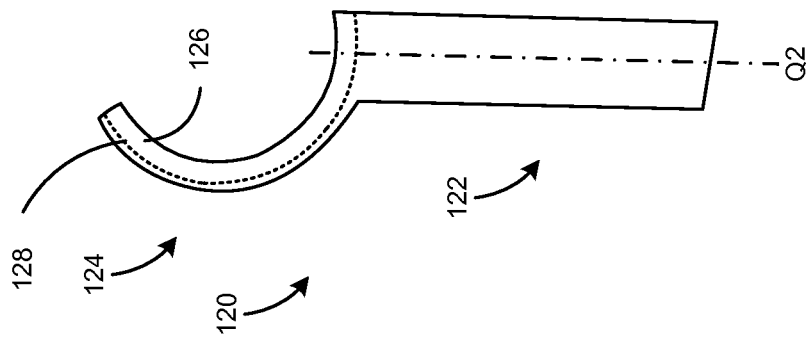
FIG. 1D is a schematic diagram that illustrates a base of the medical device shown in FIGS. 1A and 1B.
Figure 1C:
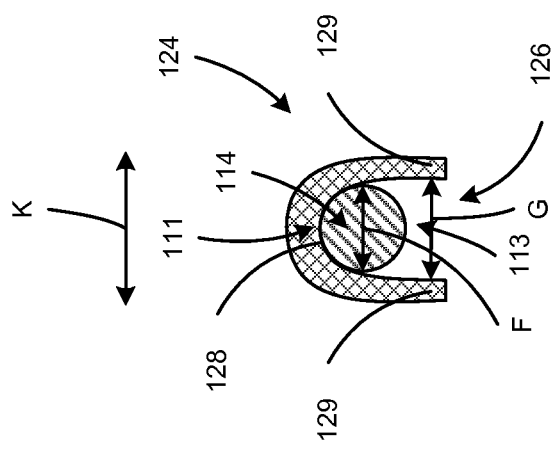
FIG. 1C is a zoomed-in cross sectional view of a channel of the medical device shown in FIGS. 1A and 1B.

FIG. 1D is a schematic diagram that illustrates the base 120 of the medical device 100 when separate from the needle member 110, which is shown in FIG. 1E. As shown in FIGS. 1A through 1E, the needle member 110 and base 120 of the medical device 100 are not hingedly coupled together. The base 120 can be made of various types of materials such as a polymer-based material (e.g., a polycarbonate material), a metal (e.g., stainless steel), and/or so forth.

In some embodiments, needle member 110 can be formed of a stainless steel material (e.g., surgical grade stainless steel). In some embodiments, the needle member 110 can be monolithically formed of a single piece of stainless steel material. Thus, the handle portion 112 of the needle member 110 and the curved portion 114 of the needle member 110 can be formed of the same material.

In some embodiments, a cross-sectional shape of the curved portion 114 of the needle member can be the same as (or substantially the same as) a cross-sectional shape (or outer profile) of the handle portion 112 of the needle member 110. For example, in some embodiments, a diameter of the curved portion 114 of the needle member can be the same as (or substantially the same as) a diameter of the handle portion 112 of the needle member 110.

In some embodiments, the needle member 110 can have a handle (not shown) made of a material that is different than the material used to make the curved portion 114 of the needle member 110. In other words, the handle portion 112 of the needle member 110 can be replaced with (or covered with) a handle that is made of a material that is different than the material used to make the curved portion 114 of the needle member 110. For example, the curved portion 114 of the needle member 110, which can be made of a surgical grade stainless steel, can be coupled to a handle made of, for example, a polymer-based material. In such embodiments, the handle can have a cross-sectional area (or outer profile) that is greater than (e.g., significantly greater than) a cross-sectional area (or outer profile) of the curved portion 114 of the needle member 110.

Although a stowed configuration and a deployed configuration are shown respectively in FIGS. 1A and 1B, in some embodiments, the medical device 100 can have a different stowed configuration and deployed configuration than shown in FIGS. 1A and 1B. For example, in some embodiments, when the medical device 100 is in the deployed configuration, the handle portion 112 of the needle member 110 can come in contact with the handle 122 of the base 120. In such embodiments, the distal portion 117 of the curved portion 114 of the needle member 110 translated out of (e.g., projected out of) the guide 124 can be longer than that shown in FIG. 1B. Thus, when medical device 100 in the deployed configuration, the angle between the longitudinal axis Q1 of the handle portion 112 and the longitudinal axis Q2 of the handle 122 can be less than that shown in FIG. 1A. In some embodiments, when the medical device 100 is in the deployed configuration, the angle between the longitudinal axis Q1 of the handle portion 112 and the longitudinal axis Q2 of the handle 122 can be greater than that shown in FIG. 1A. In some embodiments, when the medical device 100 is in the stowed configuration, an angle between the longitudinal axis Q1 of the handle portion 112 and the longitudinal axis Q2 of the handle 122 can be greater than or less than that shown in FIG. 1A.

In some embodiments, movement of the needle member 110 can be limited with respect to the base 120. For example, movement of the handle portion 112 of the needle member 110 can be limited so that the handle portion 112 of the needle member 110 may not come in contact with the handle 122 of the base 120. In such embodiments, a length of the distal portion 117 translated out of the guide 124 may be limited. In some embodiments, movement of the handle portion 112 of the needle member 110 with respect to the handle 122 of the base 120 so that only a specified length of the distal portion 117 may be translated out of the guide 124. In some embodiments, the movement of the handle portion 112 of the needle member 110 with respect to the handle 122 of the base 120 may be limited by a stop (not shown) coupled to the handle portion 112 of the needle number 110 and/or the handle 122 of the base 120.

In some embodiments, the needle member 110 and the base 120 may be lockably coupled when the medical device 100 is in the stowed configuration and/or the deployed configuration. For example, the handle portion 112 of the needle member 110 may be lockably coupled to the handle 122 of the base 120 when the medical device 100 is in the deployed configuration shown in FIG. 1B. In some embodiments, the handle portion 112 of the needle member 110 may be lockably coupled to the handle 122 of the base 120 using a mechanical device such as a latch (not shown). In some embodiments, the curved portion 114 of the needle member 110 may be lockably coupled to the guide 124 of the base 120 when the medical device 100 is in the stowed configuration shown in FIG. 1A.

In some embodiments, any portion of the medical device 100 can be formed of a biocompatible material. For example, the distal tip 116 of the needle member 110 and/or the guide 124 of the base 120 can be formed of a biocompatible material.

In some embodiments, the medical device 100 can be configured so that the medical device 100 is biased towards the stowed configuration shown in FIG. 1A. In such embodiments, a mechanism such as a spring mechanism can be disposed between the handle portion 112 of the needle member 110 and the handle 122 of the base 120 to cause the handle portion 112 to be biased away from the handle 122 in the stowed configuration shown in FIG. 1A. Accordingly, a force (e.g., a constant force) may be applied (e.g., applied against the handle portion 112) to move the handle portion 112 of the needle member 110 towards the handle 122 of the base 120 so that the medical device 100 can be in the deployed configuration shown in FIG. 1B. When the force is no longer applied, the handle portion 112 can be moved away from the handle 122 by, for example, a spring mechanism. In some embodiments, the medical device 100 can include an actuator and/or a lever configured to hold the medical device 100 in the deployed configuration.

In some embodiments, at least a portion of the needle member 110 can be formed of a flexible material. For example, a portion of the needle member 110 that remains disposed within the guide 124 when in the stowed configuration (shown in FIG. 1A) and in the deployed configuration (shown in FIG. 1B) can be configured to flex or bend. In some embodiments, at least a portion of the needle member 120 that is made of a flexible material can be biased to a specified position and/or curvature. In some embodiments, at least a portion of the needle member 110 can be formed of a flexible material so that a portion of the needle member 110 can conform to a curvature of the guide 124 (e.g., a varying curvature) as the needle member 110 is slidably moved within the guide 124.

Figure 2B:
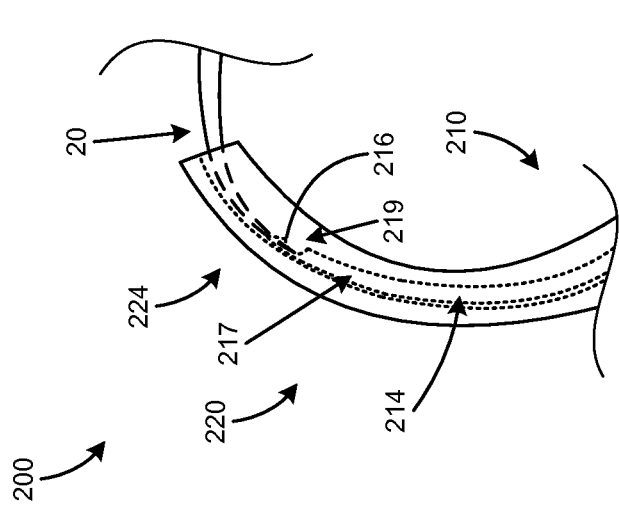
FIG. 2B is a schematic diagram that illustrates the portion of the implant coupled to the curved portion shown in FIG. 2A when the curved portion is stowed.
Figure 2A:
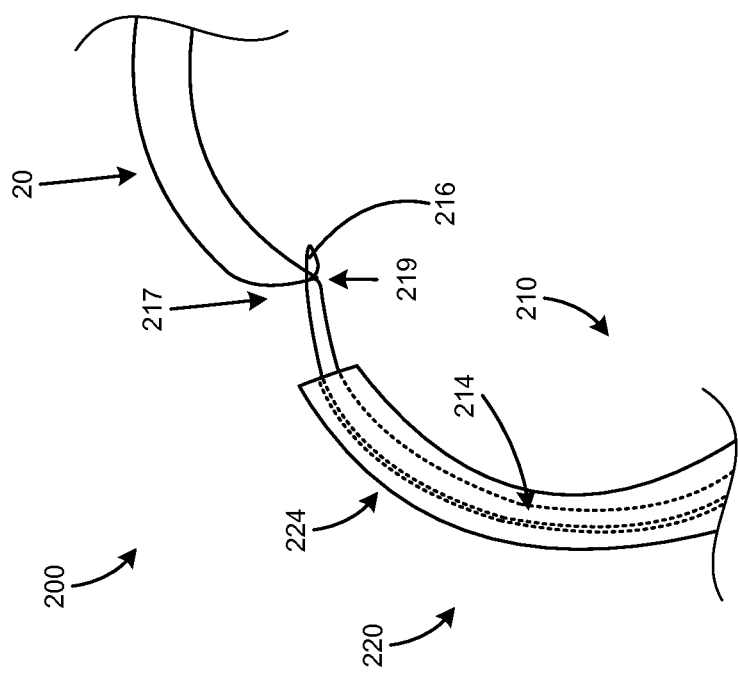
FIG. 2A is a schematic diagram that illustrates a curved portion of a needle member of a medical device coupled to a portion of an implant, according to an embodiment.

FIG. 2A is a schematic diagram that illustrates a curved portion 214 of a needle member 210 of a medical device 200 coupled to a portion 20 (e.g., a tether, a loop) of an implant, according to an embodiment. The portion 20 of the implant can be coupled to a slot 219 defined by a distal portion 217 of the curved portion 214 of the needle member 210. As shown in FIG. 2A, the portion 20 of the implant is coupled to the distal portion 217 of the curved portion 214 while the distal portion 217 of the curved portion 214 is disposed outside of a guide 224 of a base 220 of the medical device 200 in a deployed configuration. In some embodiments, the distal portion 217 can be moved outside of the guide 224 of the base 220 so that the portion 20 of the implant can be coupled to the distal portion 217.

In some embodiments, the distal portion 217 can have any type of mechanical mechanism configured to be coupled to the portion 20 of the implant. In some embodiments, the slot 219 can be, for example, an L-shaped slot or a T-shaped slot, which can be configured to receive the portion 20 of the implant to associate or couple the implant to the medical device 200. In other embodiments, the distal portion 217 can include a coupler, such as a hook or a loop, that is configured to be associated with the portion 20 of the implant or to couple the implant to the medical device 200.

FIG. 2B is a schematic diagram that illustrates the portion 20 of the implant coupled to the curved portion 214 shown in FIG. 2A when the curved portion 214 is stowed. As shown in FIG. 2B, the portion 20 of the implant is coupled to the distal portion 217 while the distal portion 217 is disposed within the guide 224 of the base 220 medical device 200. In some embodiments, the distal portion 217 can be moved from the deployed configuration shown in FIG. 2A to the stowed configuration shown in FIG. 2B (after the portion 20 of the implant has been coupled) so that the medical device 200 may be inserted into a body of the patient while in the stowed configuration with the portion 20 of the implant associated with or coupled to the medical device 200.

Figure 3:
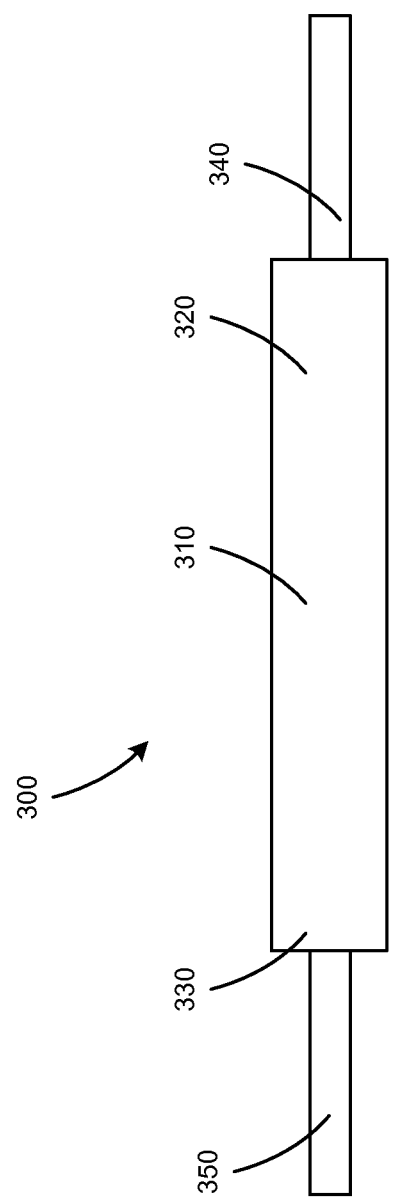
FIG. 3 is a schematic diagram of an implant, according to an embodiment.

The medical devices described herein (e.g., the medical device 100 shown in FIGS. 1A through 1E) may be used to insert an implant into a pelvic region of a patient. For example, an implant 300 as illustrated in FIG. 3 may be implanted into a pelvic region of a patient using the medical devices. The implant 300 shown in FIG. 3 is a sling and includes a support portion 310, end portions 320 and 330, and association members 340 and 350. The support potion 310 can be configured to be placed proximate a portion of the body of the patient and can be configured to provide support to the portion of the body. The end portions 330 and 340 can be configured to be placed into and coupled to bodily tissue to anchor the implant 300 within the body of the patient. The association members 340 and 350 can be configured to associate the implant 300 to the medical devices during an implantation procedure.

In some embodiments, the implant 300 may be formed of any biocompatible material. In some embodiments, the implant 300 can be formed of a mesh material. For example, the implant 300 may be formed of Advantage® mesh or the Polyform™ synthetic mesh, both as produced and/or sold by Boston Scientific Corporation. In some embodiments, in the implant 300 may be formed of a polymer material. In some embodiments, the material of the implant 300 allows for tissue in-growth to secure the implant 300 to the bodily tissue of the patient.

In some embodiments, the implant 300 can include tangs to help retain the implant 300 in place within the body of the patient. In such embodiments, the tang or tangs can be configured to engage the bodily tissue surrounding the implant 300 help retain the implant 300 in place within the body of the patient. The terms "tanged" or "tangs" as used herein mean roughened or jagged edges or areas, such as can result from cutting a woven or knit mesh material.

Figure 4B:
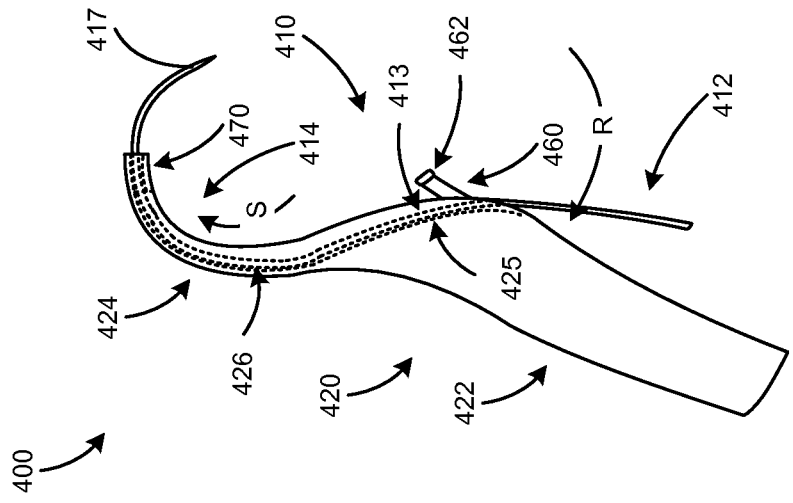
FIG. 4B is a schematic diagram that illustrates the medical device shown in FIG. 4A when the medical device is in a deployed configuration.
Figure 4A:
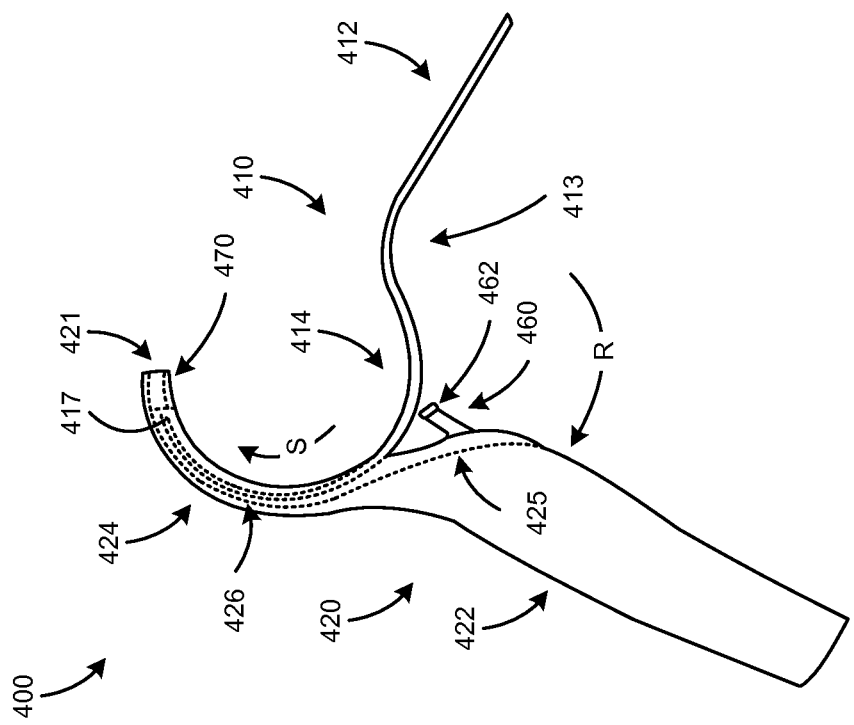
FIG. 4A is a schematic diagram that illustrates a medical device in a stowed configuration, according to an embodiment.

FIG. 4A is a schematic diagram that illustrates a medical device 400 in a stowed configuration according to an embodiment. The medical device 400 includes a needle member 410 that has a curved portion 414 configured to slidably move within a guide 424 of a base 420 along a direction S when a handle portion 412 of the needle member 410 is moved along direction R towards a handle 422 of the base 420. The medical device 400 shown in FIG. 4A is in the stowed configuration with a distal portion 417 of the needle member 410 disposed within the guide 424 of the base 420. The medical device 400 can be moved to a deployed configuration shown in FIG. 4B, when the curved portion 414 is slidably moved within the guide 424 along the direction S until at least a portion of the distal portion 417 is disposed outside of the guide 424.

As shown in FIG. 4A, the guide 424 of the base 420 defines a lumen 470 through which the distal portion 417 of the needle member 410 can move when the curved portion 414 of the needle member 410 is moved along direction S. As shown in FIG. 4A, the lumen 470 is defined within a distal portion of the guide 424. In some embodiments, the lumen 470 can be a few centimeters long (e.g., 2 cm, 4 cm). In some embodiments, the lumen 470 can be longer than that shown in FIG. 4A, or shorter than that shown in FIG. 4A. The lumen 470 can be configured to facilitate the stability of the curved portion 414 of the needle member 410 when the distal portion 417 is moved through a tissue of a patient. In some embodiments, more than one lumen (similar to lumen 470) can be defined by the guide 424 along the length of the guide 424.

In some embodiments, the lumen 470 defined by the guide 424 can have a diameter that is approximately (or slightly larger than) a diameter of the distal portion 417 of the needle member 410. In some embodiments, a distal end 421 of the guide 424 can have a diameter between a few millimeters in a few centimeters. Although not shown, in some embodiments, the guide 424 can define a lumen that is not disposed at or near the distal end 421 of the guide 424. In some embodiments, the guide 424 can define a lumen (or multiple lumen) that is disposed near the proximal end of the guide 424.

The needle member 410 in this embodiment includes a curved portion 413 disposed between the curved portion 414 and the handle portion 412 of the needle member 410. In some embodiments, the curved portion 413 can be referred to as a medial portion, the curved portion 414 can be referred to as a distal portion, and the handle portion 412 can be referred to as a proximal portion. As shown in FIG. 4A, the curved portion 413 can be curved in a direction that is different than a curvature of the curved portion 414. Specifically, a radius of curvature of the curved portion 414 can be on a different side of the needle member 410 than a radius of curvature of the curved portion 413. Thus, when viewed from, for example, the top side of the needle member 410 (when the needle member 410 is disposed within a plane as shown in FIG. 4A), the curved portion 414 has a concave curvature and the curved portion 413 has a convex curvature. When viewed from the bottom side of the needle member 410 (when the needle member 410 is disposed within a plane as shown in FIG. 8), the curved portion 414 has a convex curvature and the curved portion 413 has a concave curvature.

In some embodiments, the guide 424 of the base 420 can have a length that is longer than a length of the curved portion 424 of the needle member 420. In some embodiments, the guide 424 of the base 420 can have a length that is shorter than a length of the curved portion 424 of the needle member 420. Although not shown in FIG. 4A, any portion of the needle member 410 and any portion of the base 420 can have a helical curve.

FIG. 4B is a schematic diagram that illustrates the medical device 400 shown in FIG. 4A when the medical device 400 is in a deployed configuration. As shown in FIG. 4B, the distal portion 417 is translated outside of the guide 424 when the medical device 400 is in the deployed configuration. The medical device 400 can be moved to the deployed configuration from the stowed configuration shown in FIG. 4A, when the curved portion 414 is slidably moved within the guide 424 along the direction S until the distal portion 417 is disposed outside of the guide 424 in response to movement of the handle portion 412 of the needle member 410 along direction R towards the handle 422 of the base 420. In some embodiments, the distal portion 470 that is translated outside of guide 424 can be greater than 2 cm (e.g., 5 cm, 10 cm).

As shown in FIG. 4B, the curved portion 413 is moved into a portion 425 of the guide 424. When in the medical device 400 is in the stowed configuration, the curved portion 413 is disposed outside of the portion 425 of the guide 424. As shown in FIGS. 4A and 4B, at least a portion of the curved portion 414 of the needle member 410 is disposed within portion 426 of the guide 424 when the medical device 400 is in the stowed configuration and when the medical device 400 is in the deployed configuration.

Figure 4C:
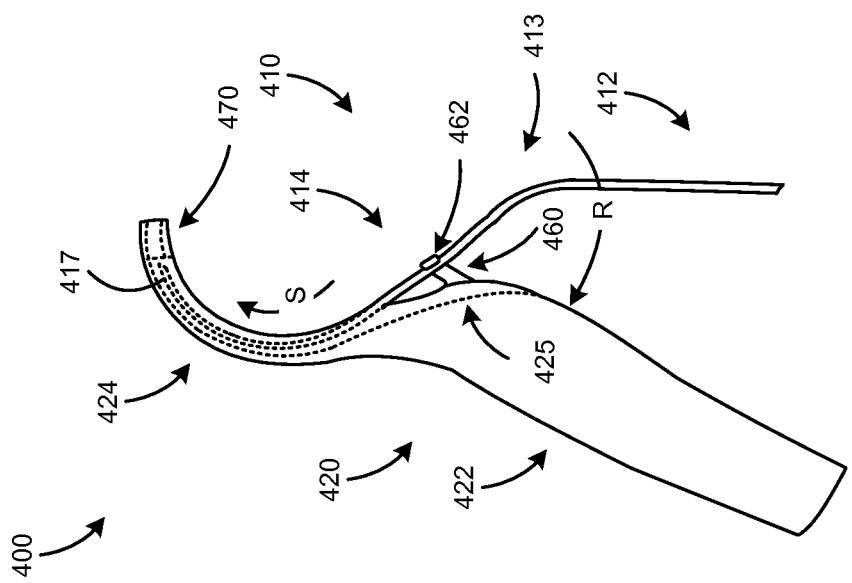
FIG. 4C is a schematic diagram that illustrates a medical device shown in FIGS. 4A and 4B when medical device is in a latched configuration.

FIG. 4C is a schematic diagram that illustrates a medical device 400 shown in FIGS. 4A and 4B when medical device 400 is in a latched configuration. As shown in FIG. 4C, the needle member 410 is coupled to a latch mechanism 460 that includes a latch 462 when medical device 400 is in the latched configuration. Thus, the needle member 410 can be configured to engage with the latch mechanism 460. In some embodiments, the latch mechanism 460 can include, for example, a hook or other type of latch device. When in the latched configuration, the distal portion 417 of the needle member 410 is disposed within the guide 424 of the base 420. In this embodiment, when medical device 400 is in the latched configuration, the curved portion 413 is not disposed within the portion 425 of the guide 424.

As shown in FIG. 4C, when the medical device 400 is in the latched configuration, the handle portion 412 of the needle member 410 is at a position closer to the handle 422 of the base 420 than a position of the handle portion 412 when the medical device 400 is in the stowed configuration (shown in FIG. 4A). The medical device 400 can be moved to the latched configuration so that the handle portion 412 of the needle member 410 may not interfere, in an undesirable fashion, with a body of a patient when the medical device 400 (e.g., leading end of the medical device 400) is being inserted into the body of the patient.

In some embodiments, the needle member 410 can be made of a relatively flexible material so that at least a portion of the needle member 410 can be coupled to the latch mechanism 460. In other words, the needle member 410 can be made of a relatively flexible material so that the medical device 400 can be moved to the latched configuration. In the embodiment shown in FIG. 4C, at least a portion of the curved portion 413 and/or at least a portion of the curved portion 414 can be bent (e.g., elastically flexed) so that the medical device 400 can be moved to the latched configuration.

Figure 5:
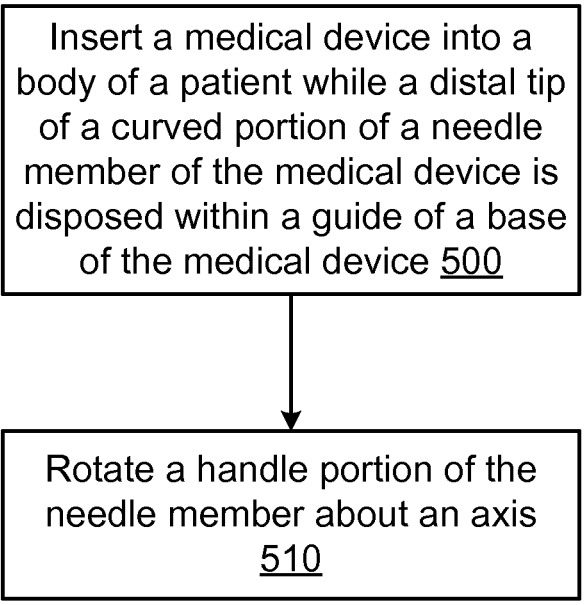
FIG. 5 is a flowchart that illustrates a method for using a medical device, according to an embodiment.

FIG. 5 is a flowchart that illustrates a method for using a medical device, according to an embodiment. As shown in FIG. 5, a medical device is inserted into a body of a patient while a distal tip of a curved portion of a needle member of the medical device is disposed within a guide of a base of the medical device (block 500). In some embodiments, the needle member and the base can collectively define a medical device. In some embodiments, the needle member can have a curved portion with a fixed curvature that is disposed within the guide of the base. In some embodiments, the needle member can have a distal portion disposed within the guide of the base. In some embodiments, the needle member can be coupled to, or associated with, an implant. In some embodiments, the curved portion of the needle member and the guide of the base can be inserted into a vaginal region of a body of the patient.

A handle portion of the needle member is rotated about an axis (block 510). In some embodiments, the handle portion of the needle member can be rotated about an axis such that the handle portion of the needle member is moved towards a handle of the base. In some embodiments, the handle portion of the needle member can be rotated about an axis such that the distal tip of the curved portion of the needle member is rotatably moved, about the axis, outside of the guide and through a tissue of the patient. In some embodiments, when the handle portion of the needle member is moved towards the handle of the base, a distal tip of the needle member can be moved through a tissue associated with an obturator foramens (e.g., an obturator muscle) of the body of the patient.

In some embodiments, when the handle portion of the needle member is moved towards the handle of the base, the needle member and the base can collectively define a deployed configuration. When in the deployed configuration, a distal portion (e.g., a distal tip) of the needle member can be disposed outside of the guide. In some embodiments, when the handle portion of the needle member is moved away from the handle the base, the needle member and the base can collectively define a stowed configuration. When in the stowed configuration, a distal portion of the needle member can be disposed within the guide.

Figure 6:
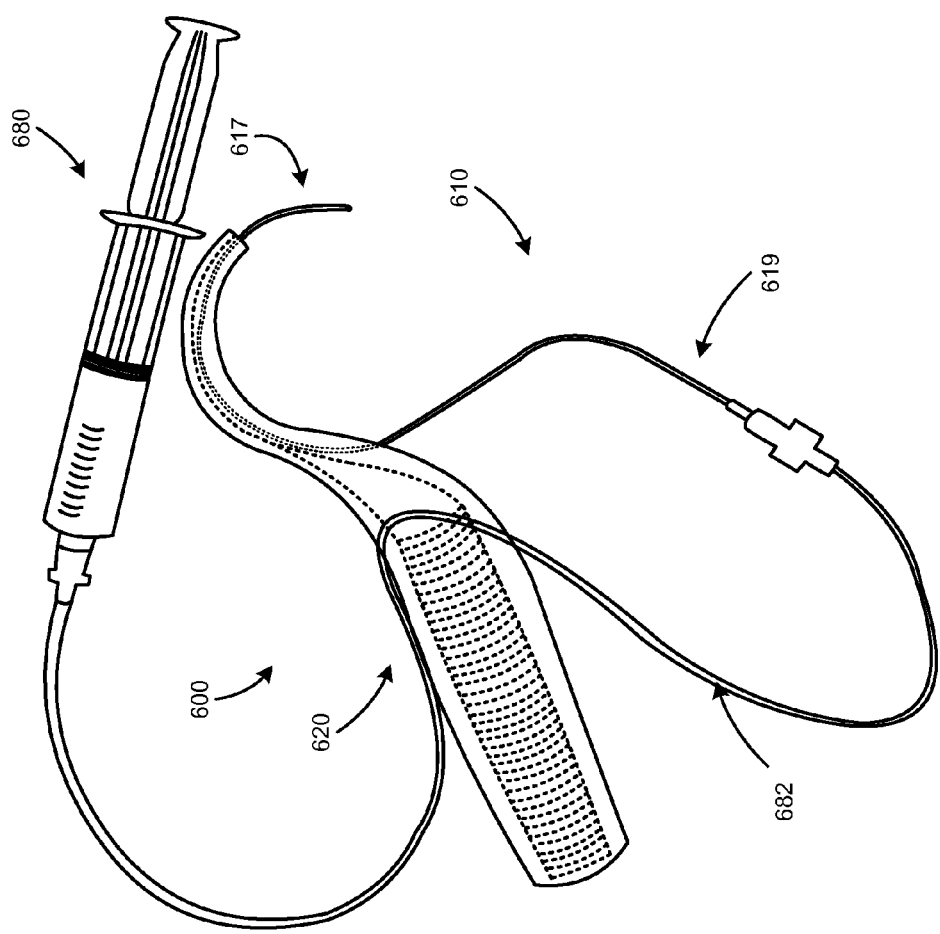
FIG. 6 is a diagram that illustrates a medical device that has a needle member configured to convey a fluid, according to an embodiment.

FIG. 6 is a diagram that illustrates a medical device 600 that has a needle member 610 configured to convey a fluid, according to an embodiment. In this embodiment, the needle member 610 can define a lumen that is configured to convey fluids to and/or from a body of a patient. In the embodiment shown in FIG. 6, the needle member 610 has a proximal portion 619 that is coupled to a syringe 680 via a tube 682. The syringe 680 is configured to deliver a fluid to and/or draw a fluid from the needle member 610 via the tube 682. In some embodiments, the syringe 680 is a 20 cc syringe. In other embodiments, the syringe 680 is larger or smaller than 20 cc. In some embodiments, a device other than a syringe may be used to move a liquid through the needle member 610.

In some embodiments, for example, a lumen defined by the needle member 610 may be used to deliver medication or anesthesia to the body of the patient during the procedure to place an implant within the body of the patient. In some embodiments, the lumen may be used to help hydro-dissect the bodily tissue during an implantation procedure. The lumen defined by the needle member 610 may be of any shape or size. For example, the cross-sectional shape (or outer profile) of the lumen may be circular, square, or rectangular.

Figure 7:
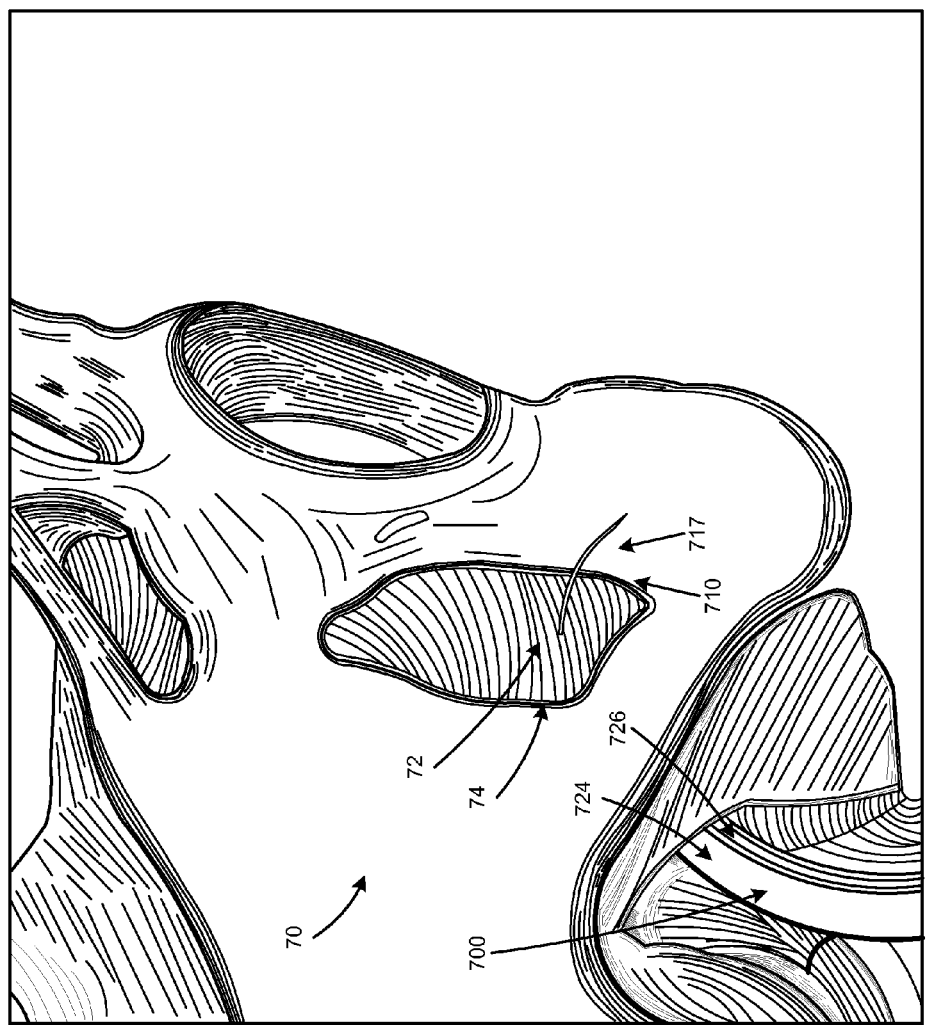
FIG. 7 is a schematic diagram that illustrates a medical device in a deployed configuration, according to an embodiment.

FIG. 7 is a schematic diagram that illustrates a medical device 700 in a deployed configuration, according to an embodiment. Specifically, a distal portion of the medical device 700 is deployed so that the distal portion 717 of the needle member 710 has pierced through tissue 72 of an obturator foramens 74 of a pelvic bone 70 of a patient. Although not shown in FIG. 7, in some embodiments, an implant can be coupled to, or associated with, the distal portion 717 of the medical device 700 so that at least a portion of the implant can be placed within the body of the patient. Although not shown in FIG. 7, in some embodiments, the distal portion 717 can be configured to pierce through additional tissue (e.g., a dermal layer) of the patient until at least a portion of the distal portion 717 is disposed outside of the patient. In such embodiments, at least a portion of an implant that may be coupled to, or associated with, the distal portion 717 can be received by a physician so that the implant may be placed (e.g., adjusted) in a desirable fashion within the body of the patient.

The needle member 710 can have at least a portion (not shown) disposed within a channel 726 of the guide 724. In some embodiments, at least a portion of the guide 724 can be pressed against at least a portion of (e.g., on top of) the pelvic bone 70 when the distal portion 717 is slidably moved out of the channel 726 of the guide 724 (from a stowed configuration (not shown)) and through the tissue 72 of the patient (to the deployed configuration shown in FIG. 7). As shown in FIG. 7, the needle member 710 (and guide 724) has a curvature that enables the needle member 710 (and guide 724) to make a predetermined turn around the pelvic bone 70 and through the obturator foramens 74.

Figure 8A:
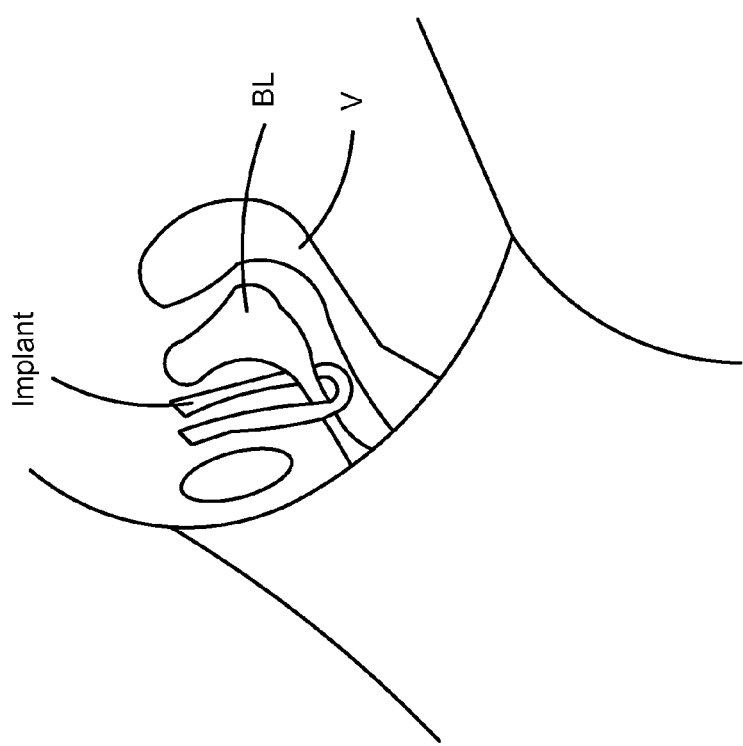

In some embodiments, as schematically illustrated in FIG. 8A, an implant (such as the implant 300 shown in FIG. 3) can be positioned, at least in part, by the medical devices described herein between a portion of a vagina V of a patient and a portion of a bladder BL of the patient such that the implant provides support to the bladder BL of the patient.

Figure 8B:
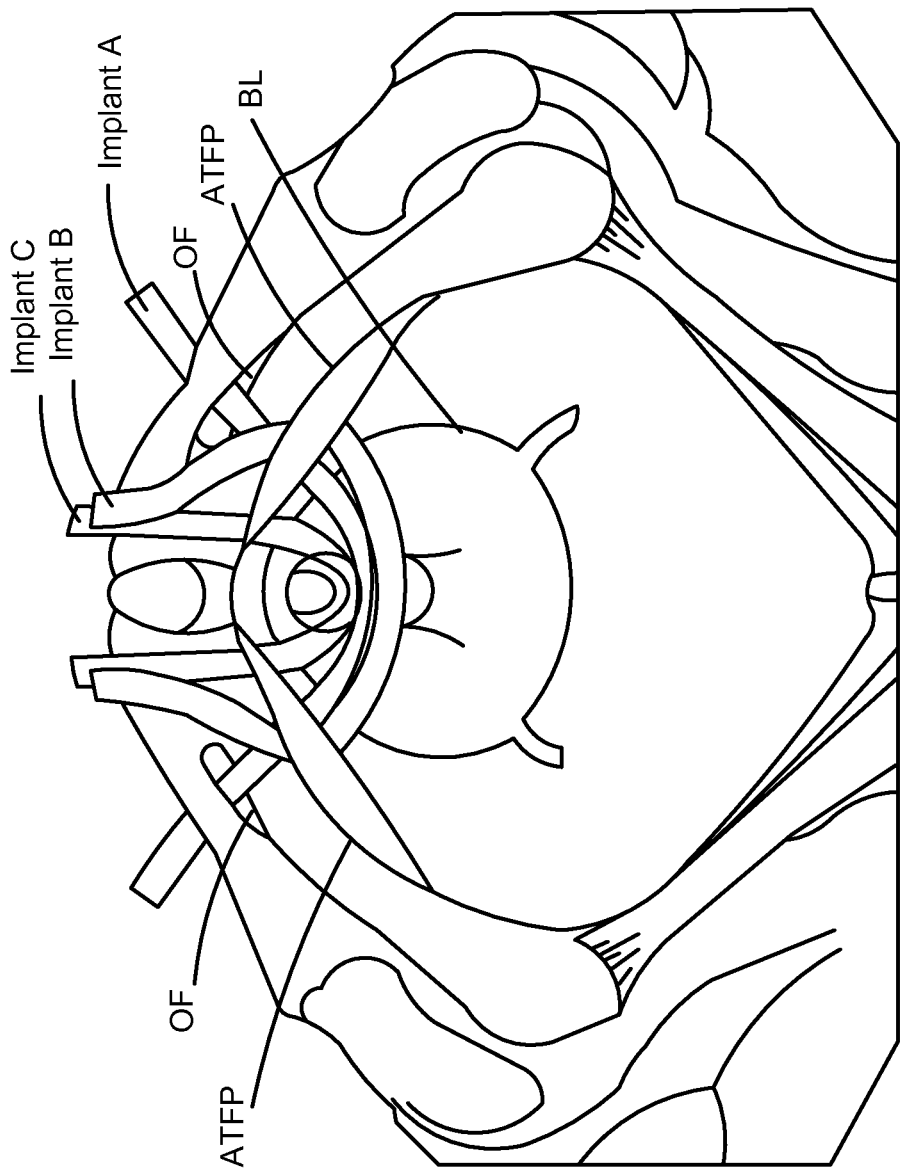

As illustrated in FIG. 8B, an implant (such as the implant 300 shown in FIG. 3) may be positioned, at least in part, by the medical devices described herein at different locations within the body of the patient. For example, as illustrated in FIG. 8B, implant A may be placed within the body of the patient such that the implant A extends through the obturator foramens OF of the patient. Alternatively, as illustrated, the implant B may extend between the ATFP (arcus tendineus facia pelvis) and the obturators of the patient. Alternatively, as illustrated, implant C may be disposed within the body of the patient in a "V" shape.

As illustrated in FIG. 8C, an implant (such as the implant 300 shown in FIG. 3) may be placed, at least in part, by the medical devices described herein such that it extends toward the obturator foramens OF of the patient, but does not extend through the obturator foramens OF. For example, the implant may be disposed within or coupled to muscles disposed proximate the obturator foramens OF. In some embodiments, the implant may be decoupled from an end of a needle member of the medical device after being placed within a desirable location within the body of the patient using a decoupling mechanism (e.g., a latch mechanism, a decoupling mechanism at an end of the needle member) controlled using, for example, a lever, trigger, and/or so forth. In some embodiments, the medical devices described herein may be used to deliver an implant to the pelvic region of the patient via a retropubic (below) or a suprapubic (above) approach.

In one general aspect, a medical device can include a base having a guide and a handle. The medical device can also include a needle member that has a curved portion and a handle portion. The curved portion of the needle member can be configured to slidably move within the guide of the base from a first position to a second position different than the first position when the handle portion of the needle member is moved towards the handle of the base.

In some embodiments, the curved portion has a distal tip that is moved from a location within the guide when the needle member is at its first position to a location outside of the guide when the handle portion of the needle member is moved towards the handle of the base. In some embodiments, an angle defined by the handle portion of the needle member and the handle of the base decreases when the handle portion of the needle member is moved towards the handle of the base. The needle member has a distal tip configured to move to a location outside of the guide and through a tissue associated of a patient when the handle portion of the needle member is moved towards the handle of the base.

In some embodiments, the needle member is in a stowed configuration within the guide when the needle member is in its first position and the needle member is in a deployed configuration outside of the guide when the needle member is in its second configuration. The medical device can also include a latch mechanism of the base configured to be coupled to at least a portion of the needle member made of a flexible material.

In some embodiments, the guide of the base has a first portion that defines a channel and the curved portion of the needle member is configured to slidably move within the channel. The guide of the base has a second portion that defines a lumen and the curved portion of the needle member has a distal tip configured to slidably move through the lumen when the handle portion of the needle member is moved towards the handle of the base.

In some embodiments, the curved portion of the needle member is configured to slidably move within the guide of the base from the first position to the second position about an axis at a radius of a substantially fixed curvature of the curved portion when the handle portion of the needle member is moved towards the handle of the base. At least a portion of the guide has a radius of a substantially fixed curvature substantially equal to the radius of the curvature of the curved portion of the needle member.

In some embodiments, the curved portion has a distal tip defining a slot configured to associate the needle member with a bodily implant and the bodily implant is configured to be disposed within a pelvic region of a patient. In some embodiments, the needle member defines a lumen therethrough and the lumen of the needle member is configured to convey a fluid.

In another embodiment, a medical device can include a base having a guide and a handle. The medical device can also include a needle member having a curved portion and a handle portion. The curved portion of the needle member configured to slidably move within the guide of the base when the handle portion of the needle member is rotatably moved within a plane towards the handle of the base about an axis orthogonal to the plane.

In some embodiments, the curved portion of the needle member has a radius of a curvature that is approximately the same as a radius of a curvature of the guide. The guide of the base has a length that is longer than a length of the curved portion of the needle member. In some embodiments, the handle portion of the needle member is aligned along a longitudinal axis that defines an acute angle with a longitudinal axis along which the handle portion of the base is aligned.

In some embodiments, the curved portion is a first curved portion, the needle member has a second curved portion. The guide has a first portion defining a concave shape, the guide has a second portion with a convex shape configured to receive the second curved portion of the needle member when the handle portion of the needle member is rotatably moved towards the handle of the base.

In some embodiments, the curved portion has a distal tip that is moved from a position within the guide to a position outside of the guide when the handle portion of the needle member is rotatably moved within the plane towards the handle of the base. In some embodiments, the curved portion has a distal tip configured to move outside of the guide and through a tissue associated with an obturator foramen of a patient when the handle portion of the needle member is rotatably moved within the plane towards the handle of the base. In some embodiments, the axis is at a radius of the curvature of the curved portion of the needle member.

In some embodiments, the curved portion is a first curved portion that has a concave shape, the needle member has a second curved portion disposed between the first curved portion and the handle portion, the second curved portion has a convex shape. In some embodiments, the curved portion and the handle portion are made of the same material.

In yet another embodiment, a method can include inserting a medical device into a body of a patient while a distal tip of a curved portion of a needle member of the medical device is disposed within a guide of a base of the medical device. The method can also include rotating a handle portion of the needle member about an axis such that the handle portion of the needle member moves towards a handle of the base and the distal tip of the curved portion of the needle member is moved outside of the guide and through a tissue of the patient.

In some embodiments, the method can include coupling, before the inserting, an implant to the needle member while the distal portion of the curved portion is disposed outside of the guide of the base. The method can also include moving, after the coupling and before the inserting, the handle portion of the needle member away from the handle of the base such that at least a portion of the implant is moved within the guide of the base.

In some embodiments, the rotating is performed at a first time, and the method can also include rotating, at a second time after the first time, the handle portion of the needle member about the axis such that the handle portion of the needle member moves away from the handle of the base and the distal tip of the needle member is moved inside of the guide and out of the tissue of the patient. The method can also include removing, after the second time, the medical device from the body of the patient while the distal tip of a needle member of the medical device is disposed within the guide of the base of the medical device.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. A medical device, comprising:
a base having a guide and a handle; and
a needle member having a curved portion defining a curvature and a handle portion, the curved portion having a distal tip, the curved portion of the needle member configured to slidably move within the guide of the base from a stowed position to a deployed position such that curved portion of the needle member moves about an axis at a radius of the curvature when the handle portion of the needle member is moved towards the handle of the base, the distal tip being disposed outside the guide of the handle when in the deployed position, the deployed position being different from the stowed position,
wherein movement from the stowed position to the deployed position is configured to cause a distance defined by a longitudinal axis of the handle portion of the needle member and a longitudinal axis of the handle of the base to decrease,
wherein, in response to the distance decreasing, the distal tip of the needle member is configured to slide out of the guide of the base,
at least a portion of the guide having a radius of a curvature substantially equal to the radius of the curvature of the curved portion of the needle member.

2. The medical device of claim 1, wherein the distal tip of the curved portion of the needle member is disposed within the guide when the needle member is in the stowed position.

3. The medical device of claim 1,
wherein the distal tip of the curved portion of the needle member is configured to move to a location outside of the guide and through a tissue associated with a patient when the handle portion of the needle member is moved towards the handle of the base.

4. The medical device of claim 1,
the medical device, further comprising:
a latch mechanism of the base configured to be coupled to at least a portion of the needle member made of a flexible material.

5. The medical device of claim 1, wherein the guide of the base has a first portion that defines a channel, the curved portion of the needle member is configured to slidably move within the channel,
the guide of the base has a second portion that defines a lumen, the distal tip of the curved portion of the needle member being configured to slidably move through the lumen when the handle portion of the needle member is moved towards the handle of the base.

6. The medical device of claim 1, wherein the curved portion of the needle member defines a slot configured to associate the needle member with a bodily implant, the bodily implant is configured to be disposed within a pelvic region of a patient.

7. The medical device of claim 1, wherein the needle member defines a lumen therethrough, and the lumen of the needle member is configured to convey a fluid.

8. A medical device, comprising:
a base having a guide and a handle, the guide having a curved portion, the handle extending from the curved portion of the guide; and
a needle member having a curved portion defining a curvature and a handle portion, the handle portion extending from the curved portion of the needle member, the curved portion of the needle member having a distal tip, the curved portion of the needle member configured to slidably move within the curved portion of the guide from a stowed position to a deployed position about an axis at a radius of the curvature when the handle portion of the needle member is moved towards the handle of the base, the stowed position being a position in which the distal tip is retracted within the curved portion of the guide, the deployed position being a position which the distal tip extends out of the curved portion of the guide, wherein movement of the handle portion of the needle member towards the handle of the base causes a distance defined by a longitudinal axis of the handle portion of the needle member and a longitudinal axis of the handle of the base to decrease, wherein, in response to the distance decreasing, the distal tip of the needle member is configured to slide out of the guide of the base, at least a portion of the guide has a radius of a curvature substantially equal to the radius of the curvature of the curved portion of the needle member.

9. The medical device of claim 8, wherein the handle portion of the needle member is linear.

10. The medical device of claim 8, further comprising:
a latch mechanism of the base configured to be coupled to at least a portion of the needle member made of a flexible material.

11. The medical device of claim 8, wherein the needle member defines a lumen therethrough, the lumen of the needle member being configured to convey a fluid.

12. The medical device of claim 8, wherein the angle defined by the longitudinal axis of the handle portion of the needle member and the longitudinal axis of the handle of the base is an acute angle in both the stowed position and the deployed position.

13. The medical device of claim 8, wherein the curved portion of the needle member includes a portion of a surface with a cross-sectional shape that matches a portion of an inner surface of the guide.

14. The medical device of claim 8, wherein the guide of the base has a length that is longer that a length of the curved portion of the needle member.

* * * * *